(12) United States Patent
Numata et al.

(10) Patent No.: US 8,968,214 B2
(45) Date of Patent: Mar. 3, 2015

(54) PROTECTOR

(75) Inventors: Shigeki Numata, Gotenba (JP);
Toshihiko Asao, Fujinomiya (JP);
Katsuhiro Shirakawa, Fujinomiya (JP);
Tomokane Kurosawa, Fuji (JP); Satoru Kanuka, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 177 days.

(21) Appl. No.: 13/074,410

(22) Filed: Mar. 29, 2011

(65) Prior Publication Data

US 2011/0178506 A1 Jul. 21, 2011

Related U.S. Application Data

(63) Continuation of application No. PCT/JP2009/064139, filed on Aug. 10, 2009.

(30) Foreign Application Priority Data

Sep. 29, 2008 (JP) .................. 2008-251835

(51) Int. Cl.
*A61M 25/00* (2006.01)
*A61M 25/09* (2006.01)

(52) U.S. Cl.
CPC ....... *A61M 25/002* (2013.01); *A61M 25/09041* (2013.01)
USPC ............................ 600/585; 600/434; 604/528

(58) Field of Classification Search
USPC .................... 600/434, 585; 604/528
See application file for complete search history.

(56) References Cited

U.S. PATENT DOCUMENTS

| | | | | |
|---|---|---|---|---|
| 5,000,698 A | * | 3/1991 | Kuzuno et al. | 439/395 |
| 5,191,888 A | * | 3/1993 | Palmer et al. | 600/434 |
| 5,651,373 A | * | 7/1997 | Mah | 600/585 |
| 5,755,695 A | * | 5/1998 | Erickson et al. | 604/164.13 |
| 5,830,157 A | * | 11/1998 | Foote | 600/585 |
| 5,978,699 A | * | 11/1999 | Fehse et al. | 600/434 |
| 6,030,349 A | * | 2/2000 | Wilson et al. | 600/585 |
| 6,190,333 B1 | * | 2/2001 | Valencia | 600/585 |

(Continued)

FOREIGN PATENT DOCUMENTS

| | | |
|---|---|---|
| JP | 3-75749 U | 7/1991 |
| JP | 10-286263 A | 10/1998 |

(Continued)

OTHER PUBLICATIONS

International Search Report (PCT/ISA/210) issued on Sep. 1, 2009, by Japanese Patent Office as the International Searching Authority for International Application No. PCT/JP2009/064139.

*Primary Examiner* — Sean Dougherty
(74) *Attorney, Agent, or Firm* — Buchanan Ingersoll & Rooney PC

(57) ABSTRACT

A protector which is used to cover a distal portion of a guide wire protruding from a distal opening of a tube body includes a first half body and a second half body which are movable between an open state and a closed state. Each of the first half body and the second half body includes a guide wire sandwiching and holding portion which mutually sandwich and hold the distal portion of the guide wire cooperatively in the closed state of the protector. Each of the first half body and the second half body also includes a tube body sandwiching and holding portion which mutually sandwich and hold the tube body cooperatively in the closed state of the protector.

21 Claims, 11 Drawing Sheets

(56) References Cited

U.S. PATENT DOCUMENTS

| | | | |
|---|---|---|---|
| D459,977 S * | 7/2002 | Byrnes et al. | D8/357 |
| 6,551,281 B1 * | 4/2003 | Raulerson et al. | 604/164.13 |
| D561,896 S * | 2/2008 | Jones | D24/130 |
| 7,341,555 B2 * | 3/2008 | Ootawara et al. | 600/106 |
| 7,717,865 B2 * | 5/2010 | Boutillette et al. | 600/585 |
| 7,886,906 B1 * | 2/2011 | Dunn | 206/364 |
| 7,951,092 B2 * | 5/2011 | Jones et al. | 600/585 |
| 8,419,680 B2 * | 4/2013 | Stenzel | 604/103.04 |
| 8,523,824 B2 * | 9/2013 | Teirstein et al. | 604/174 |
| 2003/0037439 A1 * | 2/2003 | Fujita et al. | 29/899 |
| 2005/0070820 A1 * | 3/2005 | Boutillette et al. | 600/585 |
| 2005/0178684 A1 * | 8/2005 | Kesler et al. | 206/364 |
| 2006/0094987 A1 * | 5/2006 | van Erp et al. | 600/585 |
| 2006/0253048 A1 * | 11/2006 | Jones et al. | 600/585 |
| 2007/0219467 A1 * | 9/2007 | Clark et al. | 600/585 |
| 2010/0116759 A1 * | 5/2010 | Lindgren et al. | 211/41.8 |

FOREIGN PATENT DOCUMENTS

| | | |
|---|---|---|
| JP | 2001-253472 A | 9/2001 |
| JP | 2004-290395 A | 10/2004 |

* cited by examiner

PROTECTOR

This application is a continuation of International Application No. PCT/JP2009/064139 filed on Aug. 10, 2009, and claims priority to Japanese Application No. 2008-251835 filed on Sep. 29, 2008, the entire content of both of which is incorporated herein by reference.

TECHNOLOGICAL FIELD

The present invention generally pertains to a protector used in combination with a medical device. More particularly, the invention relates to a protector for protecting a distal portion of a guide wire.

BACKGROUND DISCUSSION

Insertion of a guide wire into a blood vessel is carried out roughly in the following manner. First, a cannula is inserted into a blood vessel, followed by insertion of a guide wire into the cannula. Then, the guide wire is pushed ahead and inserted into the blood vessel.

A known guide wire supply tool (guide wire inserter) used when inserting the guide wire into a blood vessel includes: a guide wire housing portion which is constituted by a wound tube and which houses a guide wire in the lumen thereof, and a feeding-out portion which is constituted by a tube body placed at one opening portion of the guide wire housing portion and by which the guide wire passing-through the tube body is to be fed-out. An example of this is disclosed in Japanese Unexamined Patent Publication No. 2004-290395. With respect to this guide wire supply tool, when the guide wire is unused (is not fed-out yet), it becomes in a state in which the distal portion of the guide wire protrudes from the distal opening of the feeding-out portion. Therefore, the feeding-out portion is attached with a tubular cap which covers the distal portion of the guide wire from the outside thereof.

The attachment between the feeding-out portion and the cap depends on only the friction between the outer circumferential portion of the feeding-out portion and the inner circumferential portion of the cap. In the event an external force of vibration or the like acts on the cap, the cap can become detached from the feeding-out portion. When the cap is detached from the feeding-out portion, the distal portion of the guide wire protruding from the feeding-out portion may be exposed, undesirably deformed and contaminated. In addition, in a case in which an external force acts on the cap, it sometimes happens that the distal portion of the guide wire vibrates and collides with the inner circumferential portion of the cap, possibly deforming the distal portion of the guide wire.

SUMMARY

According to one aspect, a protector used to cover a distal portion of a guide wire protruding from a distal opening of a tube body comprises: a first half body and a second half body positionable in both a closed state in which an inside of the first half body faces an inside of the second half body and an open state in which the inside of the first half body and the inside of the second half body are exposed; with the first half body including a first guide wire sandwiching and holding portion and the second half body including a second guide wire sandwiching and holding portion, and with the first guide wire sandwiching and holding portion and the second guide wire sandwiching and holding portion being configured to receive the distal portion of the guide wire and sandwich and hold the distal portion of the guide wire in the closed state of the protector. The first half body includes a first tube body sandwiching and holding portion and the second half body includes a second tube body sandwiching and holding portion, wherein the first tube body sandwiching and holding portion and the second tube body sandwiching and holding portion are configured to sandwich and hold the tube body in the closed state of the protector.

Depending on the first guide wire sandwiching and holding portion and the second guide wire sandwiching and holding portion, it is possible to fix the distal portion of the guide wire. It is thus possible to inhibit or prevent the distal portion of the guide wire from being deformed unwillingly. Also, by virtue of the first tube body sandwiching and holding portion and the second tube body sandwiching and holding portion, the protector can be relatively reliably fixed with respect to the tube body, and so it is possible to inhibit or prevent the protector from being unintentionally detached from the tube body. Thus, a state of covering the distal portion of the guide wire with the protector can be maintained and concurrently, a state of being fixed to the tube body (for example, guide wire supply tool) can be maintained. It is thus possible to avoid deformation of the wire shape and deformation caused by wire movement.

It is preferable that the first guide wire sandwiching and holding portion is provided on the inside of the first half body, and the second guide wire sandwiching and holding portion is provided on the inside of the second half body.

According to one possibility, the first guide wire sandwiching and holding portion and the second guide wire sandwiching and holding portion are respectively constituted by flat surfaces facing each other in the closed state of the protector.

The first guide wire sandwiching and holding portion and the second guide wire sandwiching and holding portion preferably include a convex surface portion and a concave surface portion respectively which face each other in the closed state of the protector.

The first guide wire sandwiching and holding portion and the second guide wire sandwiching and holding portion can alternatively include a projecting portion or convex surface portion and a recessed portion or concave surface portion which face each other in the closed state of the protector, with an elastically deformable groove formed at the top portion of the projecting portion or convex surface portion.

The distal portion of the guide wire can exhibit a curved shape in the natural state in which no external force is applied, and the first guide wire sandwiching and holding portion and the second guide wire sandwiching and holding portion sandwich and hold the distal portion of the guide wire while maintaining the curved shape.

The first tube body sandwiching and holding portion is preferably provided on the inside of the first half body, and the second tube body sandwiching and holding portion is preferably provided on the inside of the second half body.

At least one of the first tube body sandwiching and holding portion and the second tube body sandwiching and holding portion includes a groove into which the tube body enters. The protector is thus fixed more reliably with respect to the tube body and is more reliably inhibited or prevented from being detached (dropped off) unwillingly. The distal portion of the guide wire is thus more reliably protected and so it is possible to more-reliably inhibit or prevent movement of the guide wire and contamination of the distal portion of the guide wire which will occur in the event the protector is detached.

It is preferable that both the first tube body sandwiching and holding portion and the second tube body sandwiching and holding portion is in the form of a groove. the grooves can be configured and arranged so that different portions in the longitudinal direction of the tube body respectively are positioned in the respective grooves.

It is preferable that the respective grooves have cross-sectional shapes different from each other. For example, in a case in which one of the grooves is positioned distally of the other, the different cross-sectional shapes make it possible to more strongly support the tube body by the groove positioned on the distal side and therefore, position deviation of the protector is inhibited or prevented.

The groove preferably positions the protector with respect to the tube body.

The protector can also be provided with a locking unit for maintaining the closed state of the protector.

The locking unit preferably includes a first engagement portion formed on the inside of one half body of the first half body and the second half body, and a second engagement portion formed on the inside of the other half body and engaged with the first engagement portion in the closed state of the protector.

The first engagement portion is preferably constituted by a convex or projecting portion and the second engagement portion is preferably constituted by a concave or recessed portion into which the first engagement portion is inserted in the closed state, and the first engagement portion is elastically deformed in the direction perpendicular to the direction toward which it is inserted with respect to the second engagement portion.

The protector preferably includes an operation unit for release-operating the close state maintained by the locking unit.

The first half body and the second half body are preferably interlinked, and there is included a rotation supporting portion for supporting one half body rotatably with respect to the other half body.

The first half body and the second half body are preferably bodies formed integrally in one piece as a single unit, and can be formed by injection molding or vacuum molding.

The tube body is preferably a body constituting a distal portion of a guide wire supply tool which can house the guide wire.

Another aspect of the disclosure here involves the combination of a guide wire, a guiding member and a protector. The guiding member comprises: a tube body possessing a distal end portion, the guide wire passing through the tube body and including a distally exposed portion extending distally beyond the distal end of the tube body. The protector comprises: a first body and a second body connected to each other, the first body and the second body being in a closed state with an inside of the first body facing an inside of the second body; the first body including a first guide wire sandwiching and holding portion, and the second body including a second guide wire sandwiching and holding portion; at least a part of the distally exposed portion of the guide wire being in contact with, and being sandwiched and held by, the first guide wire sandwiching and holding portion and the second guide wire sandwiching and holding portion; the first body including a first tube body sandwiching and holding portion and the second body including a second tube body sandwiching and holding portion, the distal end portion of the tube body being in contact with, and being sandwiched and held by, the first tube body sandwiching and holding portion and the second tube body sandwiching and holding portion. The protector in the closed state is openable to an open state so that the part of the distally exposed portion of the guide wire is no longer sandwiched and held by the first guide wire sandwiching and holding portion and the second guide wire sandwiching and holding portion, and so that the distal end portion of the tube body is no longer sandwiched and held by the first tube body sandwiching and holding portion and the second tube body sandwiching and holding portion.

According to another aspect, a method of protecting a distal portion of a guide wire protruding from a distal opening of a tube body comprises: positioning the distal portion of the guide wire which is protruding from the distal opening of the tube body between a first body and a second body while the first and second bodies are in an open state, the first body including a first guide wire sandwiching and holding portion and the second body including a second guide wire sandwiching and holding portion; and moving the first and second bodies to a closed state in which the first body overlaps the second body so that the distal portion of the guide wire is sandwiched and held between the first guide wire sandwiching and holding portion and the second guide wire sandwiching and holding portion so that the distal portion of the guide wire is protected inside the protector.

DETAILED DESCRIPTION

Several examples of the protector disclosed are described below with reference to the accompanying drawings. FIGS. 1-7 illustrate a first embodiment of the protector in connection with a guide wire assembly body. For convenience of explanation, the left or side in FIGS. 1-3 and FIG. 7 (similarly also in FIGS. 8 and 10) is referred to as the "distal end", the right side is referred to as the "proximal end", the upper side is referred to as "up", and the lower side is referred to as "down". In addition, the upper side in FIGS. 4-6 (similarly also in FIG. 9 and FIGS. 11-13) is referred to as "up" while the lower side is referred to as "down".

Figure 1:
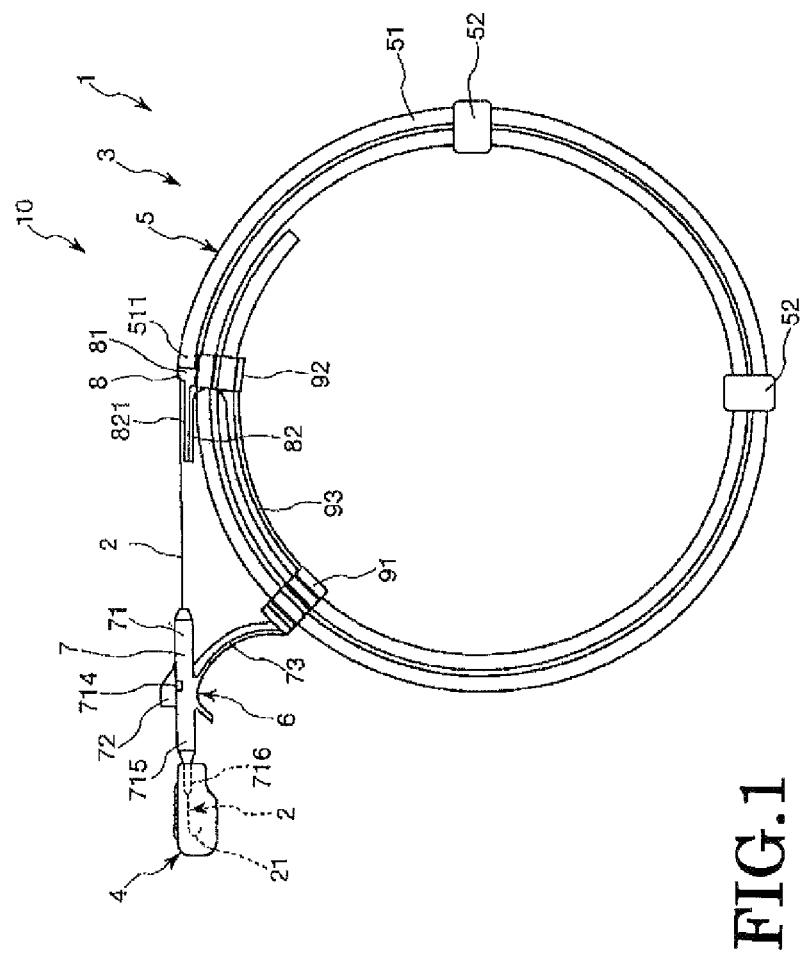
FIG. 1 is a plan view of a protector disclosed here attached to a guide wire assembly body.

As shown in FIG. 1, a protector 4 is used by being attached to a guide wire inserter (guide wire assembly body) 1 and more specifically, it protects a distal portion 21 of a guide wire 2. This guide wire inserter 1 is usually shipped in a form of a guide wire inserter 10 with a protector in which the protector 4 is attached. Also, the guide wire inserter 1 is connected to a sticking tool (not-shown) for sticking a living body, and it is a tool (apparatus) for inserting the guide wire 2 into a living body in the connection state of the guide wire (through the sticking tool).

The description below first describes the guide wire inserter 1. The guide wire inserter 1 includes the guide wire 2 and a guide wire supply tool 3 for supplying the guide wire 2.

The guide wire supply tool 3 includes a guide wire housing portion (guide wire case) 5 that houses the guide wire 2 and a feeding-out & guiding member 6 attached (fixed) to the guide wire housing portion 5 in a freely detachable manner. It is possible for this guide wire supply tool 3 to be connected to the sticking tool in a freely detachable manner by the feeding-out & guiding member 6.

As shown in FIG. 1, the guide wire housing portion 5 includes a flexible tube (tube body) 51 in which the guide wire 2 is housed (inserted) and this tube 51 is wound approximately in a ring shape (circular shape) and is bundled. More specifically, the tube 51 is wound approximately circumferentially and is bundled.

The tube 51 is held by two hold members 52 each of which has two through-holes. Each of the two through holes receives one of the windings of the tube 51 when the tube is wound in a ring shape and bundled as shown in FIG. 1. In the illustrated embodiment, the hold members 52 are clips.

The number of windings (amount of windings) of the tube 51 is not limited, though is around two turns in the example shown in the drawing.

Figure 7:
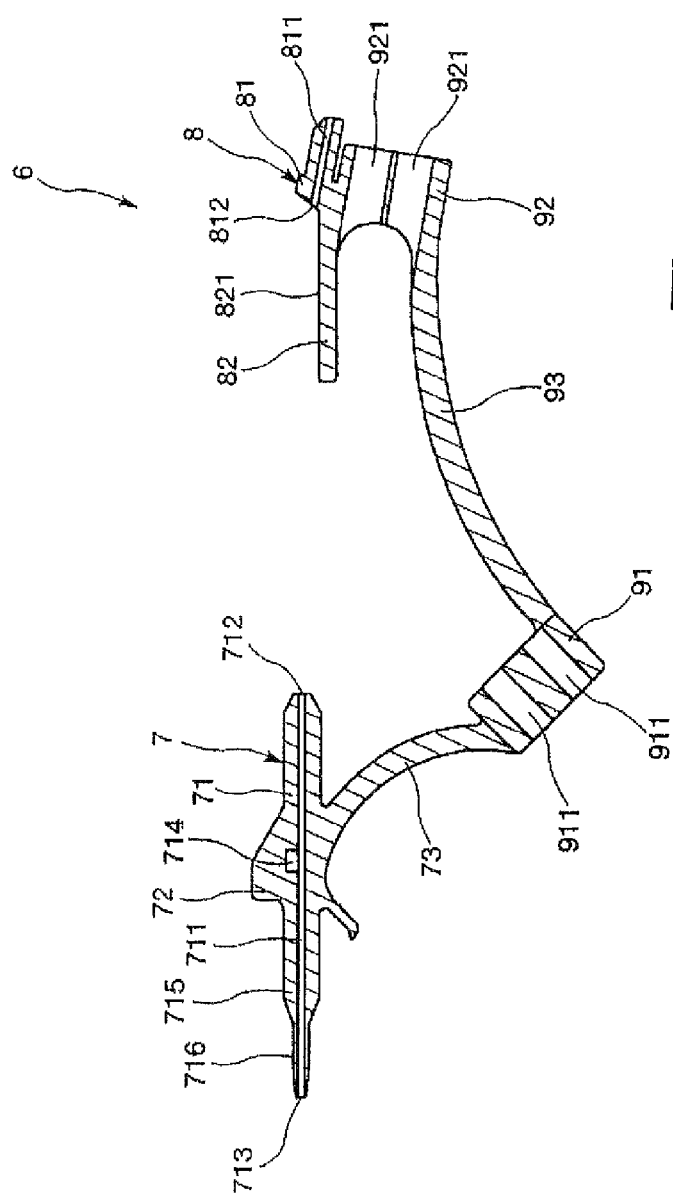
FIG. 7 is a vertical cross-sectional view of a feeding-out & guiding member of a guide wire supply tool in the guide wire assembly body shown in FIG. 1.

As shown in FIG. 7, the feeding-out & guiding member 6 includes a feeding-out portion (guide wire feeding-out portion) 8 in which the guide wire 2 housed in the guide wire housing portion 5 is fed-out and an introduction portion (guide wire introduction portion) 7 in which the guide wire 2 fed-out from the feeding-out portion 8 is received and from which the guide wire 2 is fed-out. The introduction portion 7 also serves as a guide member that guides the guide wire. The feeding-out portion 8 and the introduction portion 7 are spaced apart from each and separated by a predetermined distance.

The feeding-out portion 8 includes a cylinder-shaped feeding-out portion main body 81 and a plate-shaped pedestal (operation unit) 82, and the feeding-out portion 8 (particularly, exit 812) is positioned approximately on a circumference of the guide wire housing portion 5. An opening (distal opening) on the distal side of a hole portion (through-hole) 811 formed on this feeding-out portion main body 81 constitutes the exit 812 of the guide wire 2. The guide wire 2 passes through the hole portion 811 formed on the feeding-out portion main body 81 and is fed-out from the exit 812 toward the introduction portion 7.

The pedestal 82 protrudes from the lower side of the exit 812 and protrudes toward the entrance 712 of the introduction portion 7 described in more detail below. More specifically, the pedestal 82 is positioned in the vicinity of the guide wire 2 and the exit 812, and is located between the guide wire 2 and the guide wire housing portion 5.

The surface (top surface) of the upper side of this pedestal 82 faces the guide wire 2 and constitutes an abutment surface (facing surface) 821 on which the guide wire 2 can abut, together with a user's fingers. The guide wire 2 extends from the feeding-out portion main body 81 to the introduction portion 7.

Owing to this pedestal 82, it is possible to relatively easily carry out, for example, the operation of pulling the guide wire 2 toward the proximal side with one hand.

Also, as shown in FIG. 1, a distal portion 511 of the tube 51 is connected to (e.g., inserted into) the proximal end of the feeding-out portion main body 81 such that the hole portion 811 and the lumen of the tube 51 of the guide wire housing portion 5 communicate with each other.

The space between the feeding-out portion 8 and the introduction portion 7, more specifically the space between the distal-most end of the pedestal 82 of the feeding-out portion 8 and the proximal-most end of the introduction portion 7. and additionally the space in the vicinity thereof constitute a space (grasping space) in which the guide wire 2 is grasped and operated by a user's fingers.

Therefore, the distance between the feeding-out portion 8 and the introduction portion 7, more specifically between the distal-most end of the pedestal 82 of the feeding-out portion 8 and the proximal-most end of the introduction portion 7, is set such that fingers of a user can be inserted between the distal end of the pedestal 82 and the proximal end of the introduction portion 7.

As shown in FIG. 7, the introduction portion 7 which is positioned on the distal side of the feeding-out portion 8 includes a cylindrically-shaped (e.g., a tube body) introduction-portion main body 71. An opening on the proximal side (proximal opening) of a hole portion (through-hole) 711 formed at this introduction-portion main body 71 constitutes the entrance 712 for the guide wire 2 and an opening on the distal side (distal opening) constitutes an exit 713 for the guide wire 2. The guide wire 2 fed-out from the exit 812 of the guide wire feeding-out portion 8 passes-through the hole portion 711 at the introduction-portion main body 71. More specifically, the guide wire 2 fed-out from the guide wire feeding-out portion 8 is inserted into the entrance 712 and is fed-out from the exit 713.

Also, a distal portion 715 of the introduction-portion main body 71 includes a diameter-reduced portion (smaller-diameter portion) 716 whose outer diameter (diameter) is reduced on the distal side.

A plate-shaped wall portion (barrier) 72 is located at a center portion of the introduction-portion main body 71 and at the upper portion of the introduction-portion main body 71. The wall portion 72 possesses approximately a trapezoidal shape as seen in plan view (in FIG. 7).

A hole portion 714 is provided at the center portion of the introduction-portion main body 71 and at the upper portion of the introduction-portion main body 71. One end side of this hole portion 714 communicates with the hole portion 711 and the other end side opens toward the outside at the position corresponding to the wall portion 72 of the introduction-portion main body 71.

By virtue of the hole portion 714, in the event blood flows backward through the sticking tool while stuck in a living body, blood can escape to the outside through the hole portion 714, thus inhibiting or preventing (blocking) blood leakage toward the operation area (hand side).

Also, the wall portion 72 acts as a barrier in the event blood spouts from the hole portion 714, thus inhibiting or preventing (blocking) the scattering of the blood, particularly scattering toward the operation area.

An arm portion 73 is connected to the introduction-portion main body 71. In the illustrated embodiment, the arm portion 73 is connected to the center portion of the introduction-portion main body 71 at the lower portion of introduction-portion main body 71. A fixed portion (first fixed portion) 91 is provided at a lower end portion of the arm portion 73.

This fixed portion 91 includes two grooves 911 in which are mounted respective portions (adjacent windings) of the tube 51 of the guide wire housing portion 5 as shown in FIG. 1. The fixed portion 91 is mounted on the respective portions of the tube 51 of the guide wire housing portion 5 in a freely detachable manner. Thus, the introduction portion 7 is fixed in a freely detachable manner to the guide wire housing portion 5 through the fixed portion 91, and concurrently the tube 51 is held by the fixed portion 91 in a state of being wound and bundled in a ring shape.

A fixed portion 92 (second fixed portion) is provided at the lower portion of the feeding-out portion main body 81 of the feeding-out portion 8.

The fixed portion 92 includes two grooves 921 in which are mounted respective portions (adjacent windings) of the tube 51 of the guide wire housing portion 5 as shown in FIG. 1. The fixed portion 92 is mounted on the respective portions (adjacent windings) of the tube 51 of the guide wire housing portion 5 in a freely detachable manner. Thus, the feeding-out portion 8 is fixed in a freely detachable manner to the guide wire housing portion 5 through the fixed portion 92 at a place which is different from (spaced from) the introduction portion 7, and concurrently the tube 51 is held by the fixed portion 92 in a state of being wound and bundled in a ring shape.

The fixed portion 91 and the fixed portion 92 are coupled by a coupling portion 93. As shown in FIG. 1, this coupling portion 93 possesses an arc shape, approximately similar to the arc shape of the guide wire housing portion 5 (tube 51). More specifically, the fixed portion 91 and the fixed portion 92 are coupled through this coupling portion 93 along the arc shape of the guide wire housing portion 5 (tube 51).

Thus, it is possible to maintain the separation distance between the distal end of the pedestal 82 of the feeding-out portion 8 and the proximal end of the introduction portion 7 by a constant distance. Also, because the coupling portion 93 possesses an arc shape, the coupling portion 93 is not susceptible to becoming an obstacle.

The feeding-out & guiding member 6 is formed integrally (in one piece as a single unit) in this exemplified embodiment, but it is not limited I this regard. For example, it is also possible for the feeding-out & guiding member 6 to be formed by bonding together a plurality of members.

Also, the constituent material forming the feeding-out & guiding member 6 is not limited. Examples of materials include polyethylene, polypropylene, polyolefin of ethylene-propylene copolymer or the like, polystyrene, polycarbonate, an acrylic resin, an acrylonitrile-butadiene-styrene copolymer (ABS resin), an acrylonitrile-styrene copolymer (AS resin) or copolymers, blends, polymer alloys or like in which those above are main components.

The guide wire 2 is housed in the guide wire supply tool 3. The structure, constituent material and the like of the guide wire 2 is not limited. By way of example, it is preferable for the guide wire 2 to be a guide wire which includes a core member constituted by a super elastic body (super elastic wire) and which is provided with coils at both terminal portions of this core member.

Providing a coil at the terminal portions of the core member of the super elastic body helps impart sufficient flexibility at the terminal portions while also maintaining the diameter to be a predetermined value.

The constituent material forming the core member is not particularly limited, though it is preferable, for example, to employ a super elastic alloy such as a Ni—Ti based alloy.

The constituent material forming the coil is also not limited, though it is preferable, for example, to employ a metallic material such a stainless steel.

The outer-diameter (diameter) of the guide wire 2 is not limited to a particular dimension, though is preferably 1.0 mm or less, more preferably around 0.3 to 0.9 mm.

Figure 2:
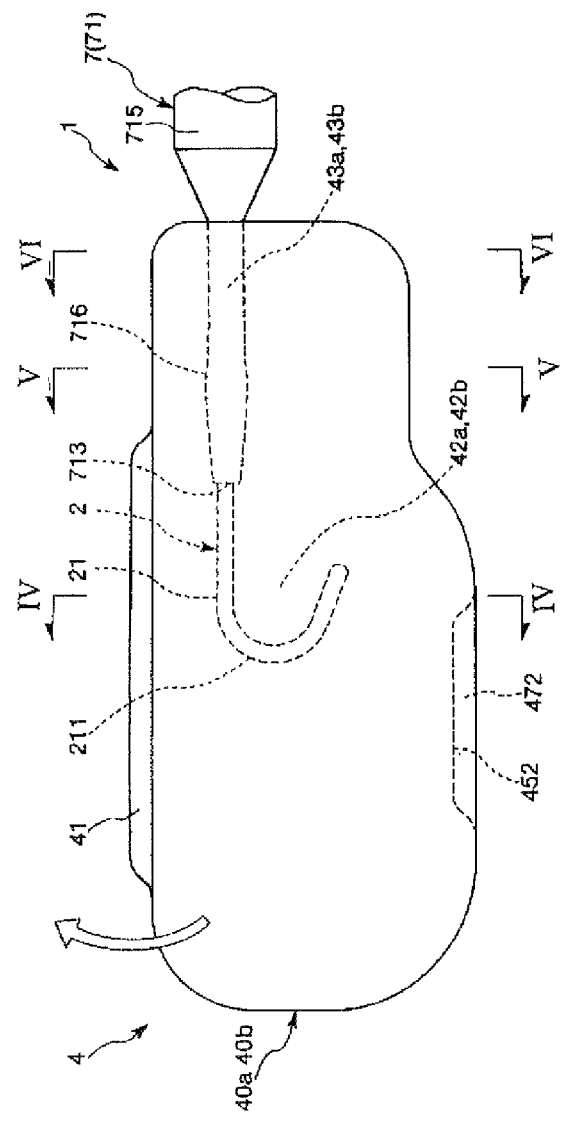
FIG. 2 is an enlarged view of the protector (in a closed state) shown in FIG. 1.

Also, in this exemplified embodiment, the distal portion 21 of the guide wire 2 possesses a curved shape, a J-shape in the illustrated embodiment, in a natural state in which not external force is applied. The shape of the distal portion 21 is not limited I this regard. As shown in FIG. 1 and FIG. 2, this distal portion 21 protrudes from the exit 713 of the introduction portion 7 (introduction-portion main body 71) in a state in which the guide wire 2 is unused (state of not yet being fed-out (supplied) from the guide wire supply tool 3).

Figure 3:
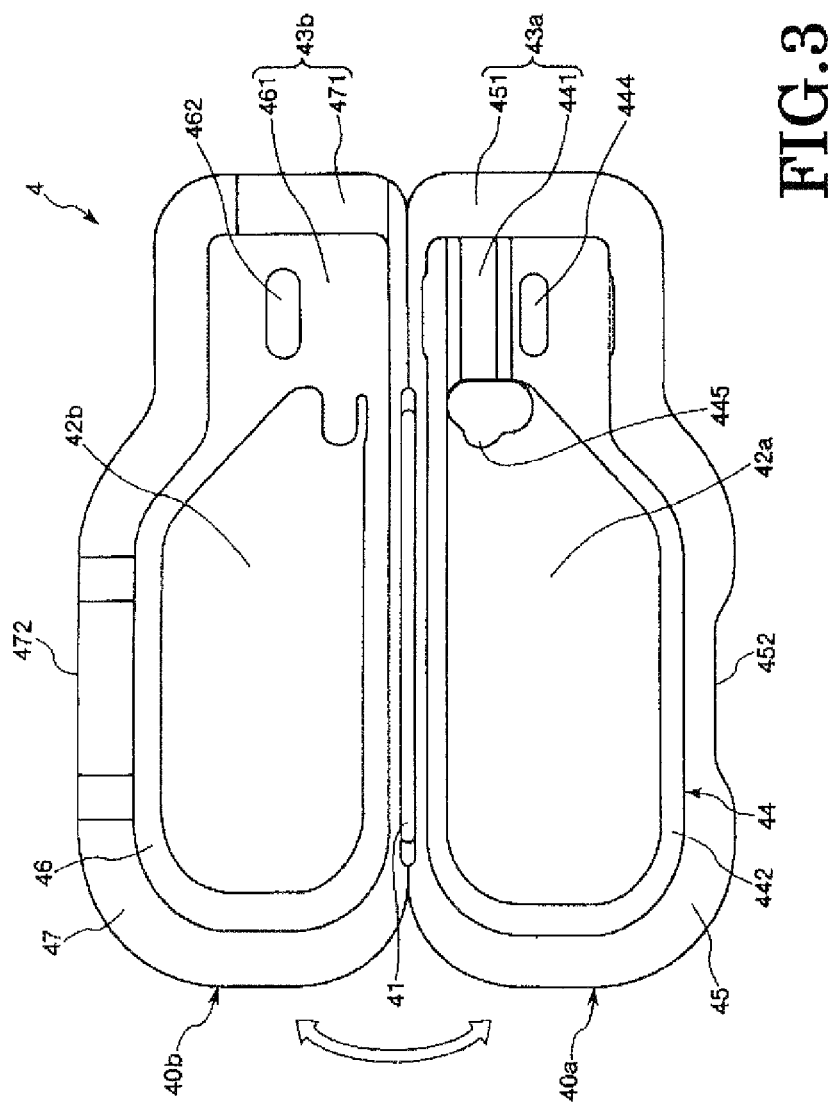
FIG. 3 is a plan view showing an open state (development state) of the protector shown in FIG. 1.

The description which follows describes the protector 4. As shown in FIG. 2 and FIG. 3, the protector 4 includes a pair of freely openable and closable bodies, namely a first body or first half body (first half-divided body) 40a and second body or second half body (second half-divided body) 40b which are coupled through a rotation supporting portion 41. As shown in FIG. 2, the protector 4 is attached to the guide wire inserter 1 in a close state and serves as a device for protecting the distal portion 21 of the guide wire 2 of the guide wire inserter 1. The first half body 40a and the second half body 40b are flat-shaped members respectively.

Figure 4:
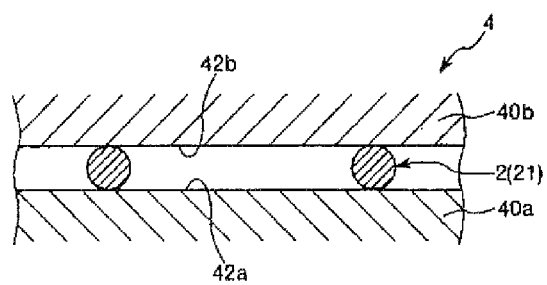
FIG. 4 is a cross-sectional view of the protector along the section line IV-IV in FIG. 2.

As shown in FIG. 4, the first half body 40a and the second half body 40b, in the closed position/state, sandwich and hold the distal portion 21 of the guide wire 2. The first half body 40a and the second half body 40b are respectively provided with a first guide wire sandwiching and holding portion 42a and a second guide wire sandwiching and holding portion 42b which mutually sandwich and hold the guide wire 2 (mounting state).

As shown in FIG. 3, the first guide wire sandwiching and holding portion 42a is in the vicinity of the center portion of the inner surface (rear surface) of the first half body 40a. This first guide wire sandwiching and holding portion 42a forms a flat surface shape.

Similarly, the second guide wire sandwiching and holding portion 42b is also in the vicinity of the center portion of the inner surface (rear surface) of the second half body 40b. This second guide wire sandwiching and holding portion 42b also forms a flat surface shape.

As shown in FIG. 4, the first guide wire sandwiching and holding portion 42a and the second guide wire sandwiching and holding portion 42b face each other when the two guide wire sandwiching and holding portions 42a, 42b are in the closed state. The distal portion 21 of the guide wire 2 is sandwiched and held between these facing guide wire sandwiching and holding portions 42a, 42b. Also, as shown in FIG. 2, with respect to the distal portion 21 of the guide wire 2, the two facing guide wire sandwiching and holding portions 42a, 42b sandwich and hold a curved portion (curved point) 211 at the distal portion 21 of the guide wire. The sandwiching and holding is thus carried out while the curved shape of the distal portion of the guide wire is maintained.

By sandwiching and holding the distal portion 21 of the guide wire 2 in this manner, it is possible to relatively reliably fix and protect the distal portion 21 of the guide wire. Thus, it is possible for the distal portion 21 to relatively reliably be inhibited or prevented from being deformed unwillingly. Of course, it should be understood that the curved distal portion 21 of the guide wire 2 is not limited to being curved in a J-shape. The first guide wire sandwiching and holding portion 42a and the second guide wire sandwiching and holding portion 42b constitute flat surfaces respectively, so that it is possible to sandwich and hold the distal portion 21 reliably without worrying about the curved shape of the distal portion 21.

Figure 5:
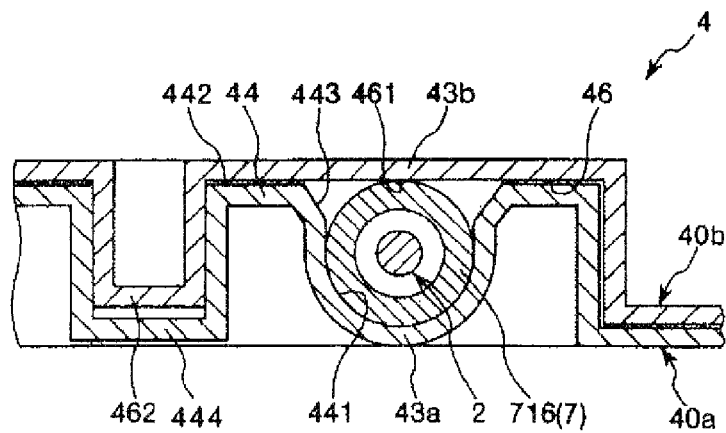
FIG. 5 is a cross-sectional view of the protector along the section line V-V in FIG. 2.
Figure 6:
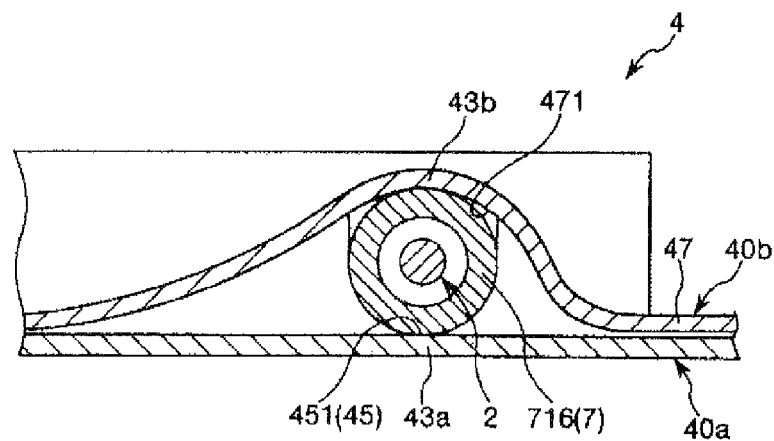
FIG. 6 is a cross-sectional view along the section line VI-VI in FIG. 2.

Also, the first half body 40a and the second half body 40b respectively include a first guiding member sandwiching and holding portion (first tube-body sandwiching and holding portion) 43a and a second guiding member sandwiching and holding portion (second tube-body sandwiching and holding portion) 43b which mutually sandwich and hold the introduction portion 7 of the feeding & guiding member 6 of the guide wire supply tool 3 in the closed state (see FIG. 2, FIG. 5 and FIG. 6). Set forth below is a more detailed discussion of the first guiding member sandwiching and holding portion 43a and the second guiding member sandwiching and holding portion 43b.

As shown in FIG. 3, the first half body 40a includes an upstanding rib or convex portion (first engagement portion) 44 that protrudes away from the adjoining portion of the first half body and surrounds almost the full circumference of the first guide wire sandwiching and holding portion 42a on the outer circumferential side of the first guide wire sandwiching and holding portion 42a. A first groove 441 is formed in the portion of the rib 44 on the right side (proximal side) in FIG. 3. The first groove 441 extends along the longitudinal direction of the first half body 40a. As shown in FIG. 5, the first groove 441 has an arc-shaped cross-sectional shape, and the diameter-reduced portion 716 of the introduction portion 7 is positioned in the first groove 441. A chamfering portion 443 is formed at the inside upper portion of the first groove 441. Thus, when inserting the diameter-reduced portion 716 of the introduction portion 7 into the first groove 441, the diameter-reduced portion 716 of the introduction portion 7 is guided by the chamfering portion 443 and it is possible to carry out the insertion operation relatively easily. Also, the outer circumferential side of the rib 44 is provided with a flat surface portion 45 forming a flat surface shape surrounding almost the full circumference of the rib 44. The flat surface portion 45 is arranged rearwardly of (to the right in FIG. 3) the top surface 442 of the rib 44.

The second half body 40b includes a concavely recessed concave portion (second engagement portion) 46 surrounding almost the full circumference of the second guide wire sandwiching and holding portion 42b on the outer circumferential side of the second guide wire sandwiching and holding portion 42b. This concave portion 46 faces the rib 44 of the first half body 40a in the closed state. That is, the concave portion 46 is a portion into which the rib 44 is inserted as illustrated in FIG. 5. Also, an upstanding rib (second convex portion) 47 is provided on the outer circumferential side of the concave portion 46. The rib 47 protrudes away from the adjoining portion of the second half body 40b and surrounds almost the full circumference of the concave portion 46. This rib 47 is, in the closed state, a region facing the flat surface portion 45 of the first half body 40a. The portion of the rib 47 on the right side (proximal side) in FIG. 3 is provided with a second groove 471 extending along the longitudinal direction of the second half body 40b. As shown in FIG. 6, the second groove 471 possesses an arc-shaped cross-section shape, and the diameter-reduced portion 716 of the introduction portion 7 is positioned in the second groove 471.

As shown in FIG. 5, in the closed state, the diameter-reduced portion 716 of the introduction portion 7 is located in the first groove 441 of the first half body 40a and further, the diameter-reduced portion 716 of this introduction portion 7 is sandwiched and held between the first groove 441 and a portion of the concave portion 46 of the second half body 40b (hereinafter, this portion is referred to as "sandwiching and holding function portion 461"). As also shown in FIG. 6, in the closed state, the diameter-reduced portion 716 of the introduction portion 7 is located in the second groove 471 of the second half body 40b and further, the diameter-reduced portion 716 of this introduction portion 7 is sandwiched and held between the second groove 471 and a portion of the flat surface portion 45 of the first half body 40a (hereinafter, this portion is referred to as "sandwiching and holding function portion 451").

By sandwiching and holding the diameter-reduced portion 716 of the introduction portion 7 in this manner, the protector 4 is relatively reliably fixed with respect to the diameter-reduced portion 716 of the introduction portion 7 and it is reliably inhibited or prevented from being detached (dropped off) unwillingly. Thus, it is possible to quite reliably protect the distal portion 21 of the guide wire 2, and it is therefore possible to relatively reliably inhibit or prevent movement of the guide wire 2 and contamination of the distal portion 21 which may occur in a case in which the protector 4 is detached.

In the protector 4 described above, the first guiding member sandwiching and holding portion 43a is constituted by a groove (e.g., the first groove 441) and the sandwiching and holding function portion 451, and the second guiding member sandwiching and holding portion 43b is constituted by a groove (e.g., the second groove 471) and the sandwiching and holding function portion 461 (see FIG. 3).

As also shown in FIG. 3, the first groove 441 and the second groove 471 are arranged at different positions in the longitudinal direction of the protector 4. This facilitates the different portions in the longitudinal direction of the diameter-reduced portion 716 of the introduction portion 7 entering into the first groove 441 and the second groove 471 respectively. That is, the part of the diameter-reduced portion 716 (distal portion of the tube body) positioned in the first groove 441 is longitudinally shifted relative to the part of the diameter-reduced portion 716 (distal portion of the tube body) positioned in the second groove 471. The diameter-reduced portion 716 of the introduction portion 7 is thus sandwiched and held from the opposing directions, thus increasing the sandwiching and holding force.

As shown in FIG. 5 and FIG. 6, the first groove 441 and the second groove 471 possess different curvature-factors (reciprocal of the radius of curvature). More specifically, the curvature-factor of the first groove 441 is larger than the curvature-factor of the second groove 471. Thus, it is possible to relatively strongly support the diameter-reduced portion 716 of the introduction portion 7 by the first groove 441 which is the side (distal side) nearer to the distal portion 21 of the guide wire 2 and therefore, position deviation of the protector 4 is inhibited or prevented. In other words, positioning of the protector 4 with respect to the guide wire inserter 1 (tube body) can be accomplished as desired. Thus, it is possible for the protector 4 to more reliably protect the distal portion 21 of the guide wire 2. Also, the reason the curvature-factor of the second groove 471 is smaller is to prevent a burr and deformation during molding.

As mentioned above, in the closed state, the rib 44 of the first half body 40a is positioned in the concave portion 46 of the second half body 40b as illustrated in FIG. 5. At that time, the rib 44 of the first half body 40a is tightly fitted in the concave portion 46 of the second half body 40b. The frictional force helps maintain the closed state between the outer surface of the rib 44 and the inner surface of the concave portion 46. Thus, the closed state (sandwiching and holding state with respect to the guide wire inserter 10 with a protector) of the protector 4 is relatively dependably maintained and so it is possible to avoid a phenomenon in which the protector 4 is unintentionally opened and is detached from the guide wire inserter 1. In this manner, the protector 4 is outfitted with a closed state maintaining unit (locking unit) that maintains the closed state of the protector 4 and that is constituted by the rib 44 of the first half body 40a and the concave portion 46 of the second half body 40b.

Also, as shown in FIG. 3, in the vicinity of the first groove 441 of the first half body 40a, there is arranged a small concave portion 444 formed by concavely recessing a portion of the rib 44. On the other hand, in the vicinity of the sandwiching and holding function portion 461 of the second half body 40b, there is arranged a small convex portion 462 in which a portion of the concave portion 46 is upstanding (protrudes). As shown in FIG. 5, in the closed state, the small convex portion 462 is positioned in and engaged with the small concave portion 444. This thus assists with maintaining the closed state provided by the rib 44 of the first half body 40a and the concave portion 46 of the second half body 40b and so the closed state is more reliably kept. Also, the sandwiching and holding force between the first guiding member sandwiching and holding portion 43a and the second guiding member sandwiching and holding portion 43b increases.

When release-operating the closed state maintained by the close state maintaining unit (when changing the protector 4 from the closed state to the open state), it is possible, by placing fingers on an operation unit 472 formed on the rib 47 (outer circumferential portion) of the second half body 40b and by operating the second half body 40b to be rotated around the rotation supporting portion 41, to relatively easily carry out the release-operation or opening operation. Generally speaking, the operation unit is constituted by a peripheral portion of one of the first and second half bodies extending outwardly beyond the outer periphery of the overlapping portion of the other of the first and second half bodies. In the illustrated embodiment, a notched portion 452 is formed in the flat surface portion 45 (circumferential portion) of the first half body 40a. This notched portion 452 is located along a side of the first half body 40a opposite the side at which the rotation supporting portion 41 is located. In the closed state, a portion of the rib 47 of the second half body 40b is exposed beyond or through this notched portion 452. This exposed portion constitutes the operation unit 472. In the guide wire inserter 10 with the protector, in case of connecting the guide wire inserter 1 to the sticking tool, the above release-operation is carried out and the protector 4 is removed.

The rotation supporting portion 41 is the portion at which the first half body 40a is coupled to the second half body 40b, and rotatably supports one side of one half body with respect to one side of the other half body. In this exemplified embodiment, the rotation supporting portion 41 rotatably supports the second half body 40b with respect to the first half body 40a. The rotation supporting portion 41 is constituted by a thin-thickness portion which is thinner than the thicknesses of the adjoining portions of the first half body 40a and the second half body 40b. Owing to the fact that this rotation supporting portion 41 is deformed by being bent, it is possible to open and close the protector 4 relatively easily and reliably.

Also, it is preferable for the first half body 40a, the second half body 40b and the rotation supporting portion 41 to be formed integrally, in one piece and at the same time by injection molding or vacuum molding. Thus, it is possible to comparatively easily manufacture the protector 4 having the features and construction described above.

The constituent material forming the protector 4 is not limited to a particular material. It is possible to use, for example, the material discussed above in the explanation of the materials to be used to fabricate the feeding-out & guiding member 6. It is also possible to construct the protector 4 to be constructed so that the interior of the protector is visible.

In order to attach the protector 4 having the construction described above to the guide wire inserter 1, the following procedure is preferably employed.

First, the protector 4 is in the open state. I this open state, the introduction portion 7 of the guide wire inserter 1 is then inserted into the first groove 441 of the first half body 40a until the exit 713 at the distal-most end of the diameter-reduced portion 716 contacts the distal end (stopper) 445 of the first groove 441. Also, the amount by which the distal portion 21 protrudes distally beyond the exist 713 is adjusted such that the distal portion 21 of the guide wire 2 of the guide wire inserter 1 is positioned on the first guide wire sandwiching and holding portion 42a.

Next, the second half body 40b is rotated toward the first half body 40a and a closed state of the protector is obtained. Thus, it is possible to mount the protector 4 to the guide wire inserter 1 and concurrently, it is possible to fix the distal portion 21 of the guide wire 2.

Figure 8:
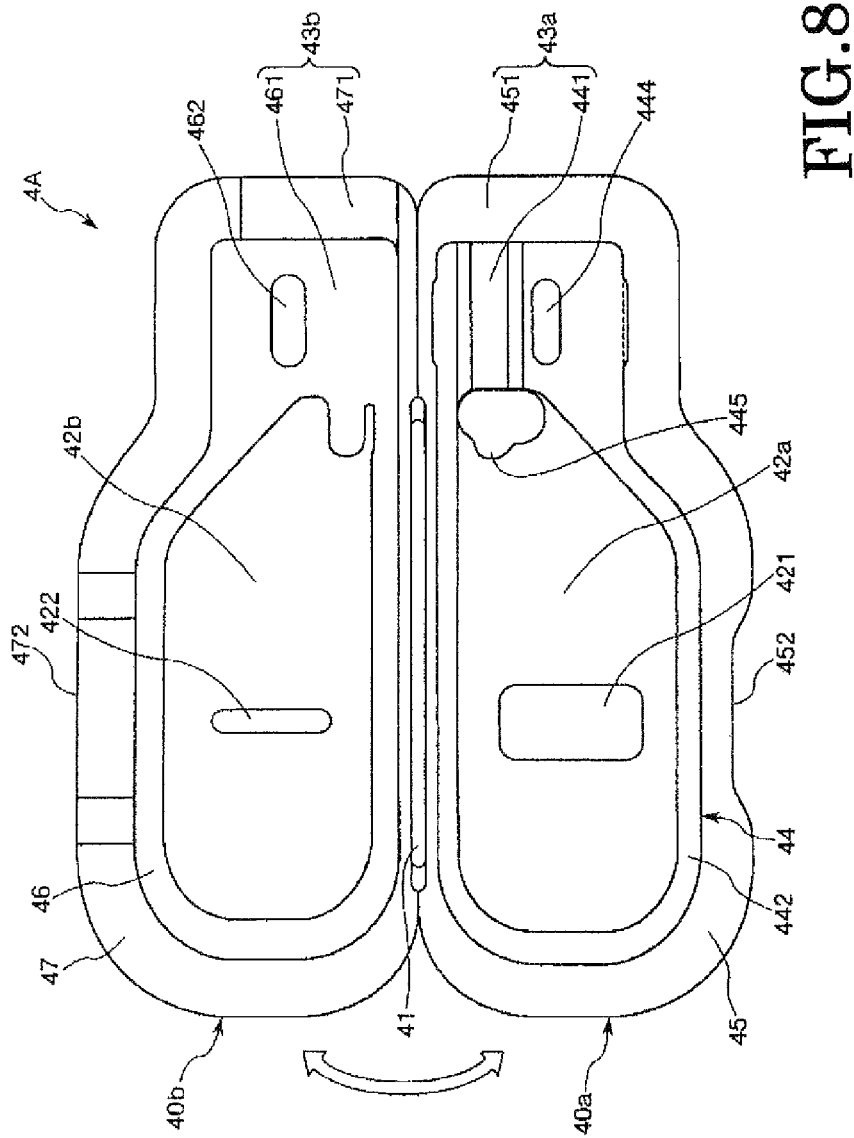
FIG. 8 is a plan view of a second exemplified embodiment of a protector (in an open state) disclosed here.
Figure 9:
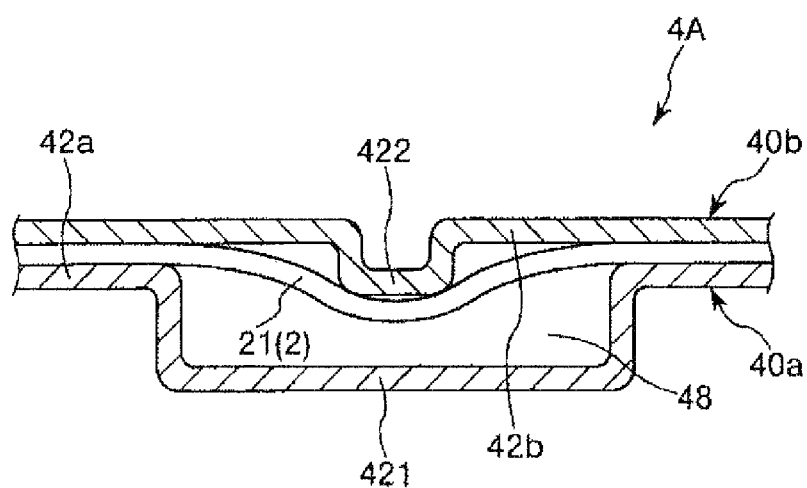
FIG. 9 is a vertical cross-sectional view in a closed state of a concave portion and a convex portion of the protector shown in FIG. 8.

FIGS. 8 and 9 illustrate a second exemplified embodiment of the protector 8. In FIG. 8, the protector is shown in the open state and the guide wire is omitted.

The following description of the second embodiment of the protector focuses primarily on aspects of the protector different from those associated with the first embodiment described above. Features of the protector that are the same as in the first embodiment are identified by the same reference numerals and a detailed description of such features is not be repeated.

This second exemplified embodiment is similar to the first exemplified embodiment, except for the construction of the first guide wire sandwiching and holding portion and the second guide wire sandwiching and holding portion.

The second embodiment of the protector 4A shown in FIG. 8 includes a recessed portion or concave portion (concave surface portion) 421 which is concavely recessed on the first guide wire sandwiching and holding portion 42a of the first half body 40a. The second half body 40b is provided with an upstanding protrusion or convex portion (convex surface portion) 422 which protrudes on the second guide wire sandwiching and holding portion 42b. As shown in FIG. 9, in the closed state, the convex portion 422 is positioned in the concave portion 421. Thus, a portion of the distal portion 21 of the guide wire 2 is sandwiched between the convex portion 422 and the concave portion 421, and the sandwiching and holding force with respect to the guide wire 2 increases. Consequently, the guide wire 2 is sandwiched and further reliably held by the first guide wire sandwiching and holding portion 42a and the second guide wire sandwiching and holding portion 42b.

Figure 10:
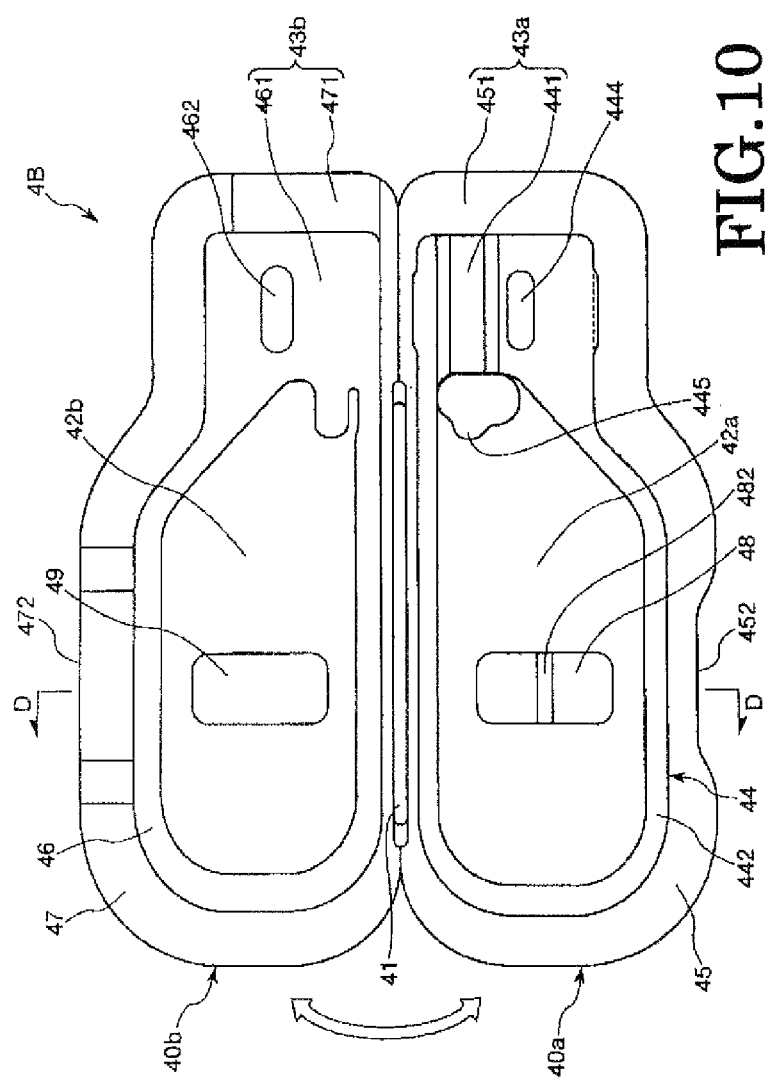
FIG. 10 is a plan view showing a third exemplified embodiment of a protector (in an open state) disclosed here.
Figure 11:
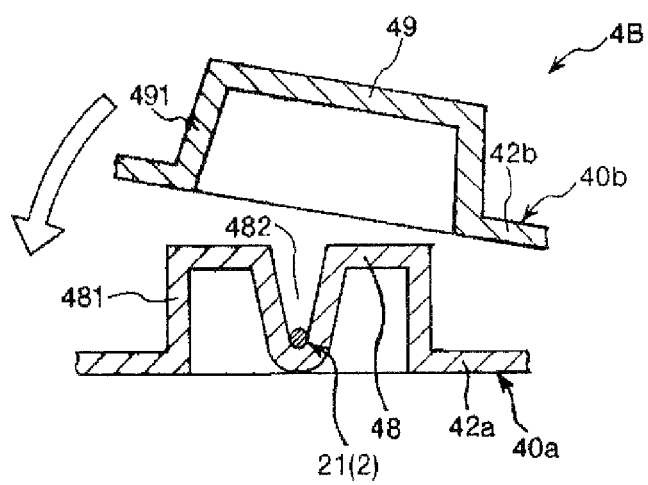
FIG. 11 is a diagram showing a process from an open state to a closed state at the cross-section indicated by the section line XI-XI in FIG. 8.
Figure 12:
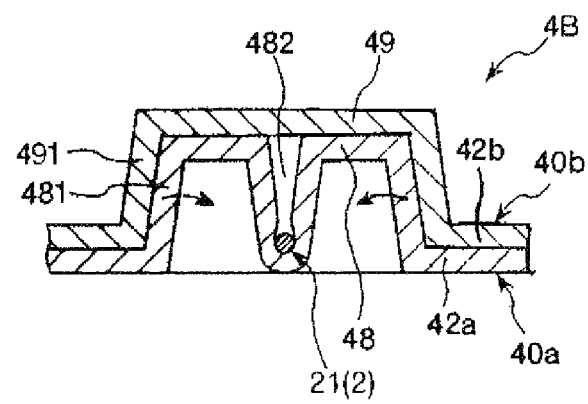
FIG. 12 is a diagram showing a process from an open state to a close state at the cross-section indicated by the section line XI-XI.

FIGS. 10-12 illustrate a third exemplified embodiment of the protector. In FIG. 10, the protector is shown in the open state and the guide wire is omitted.

The following description of the third embodiment of the protector focuses primarily on aspects different from those associated with the embodiments described above. Features of the protector that are the same as in the embodiments described above are identified by the same reference numerals and a detailed description of such features is not be repeated.

This exemplified embodiment is similar to the second exemplified embodiment, except for the construction of the first guide wire sandwiching and holding portion and the second guide wire sandwiching and holding portion.

The third embodiment of the protector 4B shown in FIG. 10 includes an upstanding protrusion or convex portion (convex surface portion) 48 which protrudes from the first guide wire sandwiching and holding portion 42a for the first half body 40a. The second half body 40b includes a recessed portion or concave portion (concave surface portion) 49 which is concavely recessed on the second guide wire sandwiching and holding portion 42b. As shown in FIG. 12, in the closed state, the convex portion 48 is positioned in and engages this concave portion 49. Thus, maintaining the closed state by virtue of the rib 44 of the first half body 40a and the concave portion 46 of the second half body 40b is assisted and so the closed state is maintained more reliably. Also, the sandwiching and holding force between the first guide wire sandwiching and holding portion 42a and the second guide wire sandwiching and holding portion 42b is increased.

As shown in FIGS. 11 and 12, an elastically deformable groove 482 is formed at a top portion of the convex portion 48 of the first half body 40a. This groove 482 extends along the longitudinal direction of the first half body 40a and receives a portion of the distal portion 21 of the guide wire 2. As the protector 4B is moved from the open state to the closed state, the projection or convex portion 48 moves from the state shown in FIG. 11 to the state shown in FIG. 12, whereby the projection or convex portion 48 is received in the recessed portion or concave portion 49. As the convex portion 48 moves from the FIG. 11 state to the FIG. 12 state, respective wall portions 481 of the convex portion 48 are depressed inwardly toward each other in the directions of the arrows in FIG. 12 (directions perpendicular to the insertion direction with respect to the concave portion 49) caused by the inclined wall portion 491 of the concave portion 49, and the space between the wall portions 481 becomes narrower (becomes in a state of being narrowly-sandwiched). Thus, in the state shown in FIG. 12 (in the closed state of the protector), the distal portion 21 of the guide wire 2 is strongly sandwiched and held by the groove 482 and a sandwiching and holding state with respect to the guide wire 2 is maintained.

Figure 13:
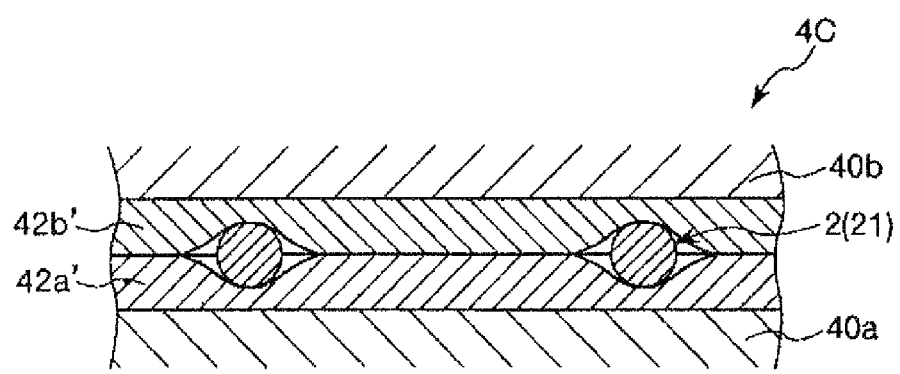
FIG. 13 is a horizontal cross-sectional view of a fourth exemplified embodiment of a protector (in a closed state) disclosed here.

FIG. 13 illustrates a fourth exemplified embodiment of a protector (in a closed state). The following description of the fourth embodiment of the protector focuses primarily on aspects different from those associated with the embodiments described above. Features of the fourth embodiment of the protector that are the same as in the embodiments described above are identified by the same reference numerals and a detailed description of such features is not be repeated.

This fourth exemplified embodiment is similar to the first exemplified embodiment, except for the construction of the first guide wire sandwiching and holding portion and the second guide wire sandwiching and holding portion.

In the protector 4C shown in FIG. 13, the inside of the first half body 40a is provided with a first guide wire sandwiching and holding portion 42a' having flexibility. Also, the inside of the second half body 40b is provided with a second guide wire sandwiching and holding portion 42b' having flexibility.

In such a protector 4C, with the protector in the closed state shown in FIG. 13, the first guide wire sandwiching and holding portion 42a' and the second guide wire sandwiching and holding portion 42b' are compressed in the area of the distal portion 21 of the guide wire 2, thus providing a tight fit. Thus, it is possible to sandwich & hold and to protect the distal portion 21 of the guide wire 2 more reliably.

It should be noted that it is possible for each of the first guide wire sandwiching and holding portion 42a' and the second guide wire sandwiching and holding portion 42b' to be constituted, for example, by a non-skid sheet member composed of an elastic body or a porous body.

The protector disclosed here is described above by way of several embodiments. It is possible for the respective portions constituting the protector to be replaced by portions having other constructions performing similar functions. Also, features other than those described above can be added.

Also, the various protectors can embody features from the other examples of embodiments disclosed here.

The protector is not limited to a protector for protecting the distal portion of the guide wire protruding from the introduction portion of the guide wire supply tool. For example, it is also possible for the protector to be a protector that protects the distal portion of the guide wire protruding from a tube body for medical use such as a sheath, a catheter and the like.

The inside of the protector can also be provided with an antiskid unit for preventing skidding with respect to the guide wire inserter. The form of this antiskid unit is not limited. As one example, a roughening process can be applied on the inner surfaces of the first half body and the second half body. According to another example, elastic sheet members can be fixed on the inner surfaces of the first half body and the second half body.

The protector described here is a protector used to cover a distal portion of a guide wire protruding from a distal opening of a tube body, and the protector includes: a pair of a first half body and a second half body which can open and close freely, wherein each of the first half body and the second half body includes a first guide wire sandwiching and holding portion and a second guide wire sandwiching and holding portion which mutually sandwich and hold the distal portion of the guide wire cooperatively in a close state, and a first tube body sandwiching and holding portion and a second tube body sandwiching and holding portion which mutually sandwich and hold the tube body cooperatively in the close state. Consequently, it is possible to fix the distal portion of the guide wire quite reliably.

The detailed description above describes features and aspects of embodiments of a protector. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A combination of a guide wire, a guiding member and a protector, the guiding member comprising: a tube body possessing a distal end portion, the guide wire passing through the tube body and including a distally exposed portion extending distally beyond the distal end of the tube body, the protector comprising: a first body and a second body connected to each other, the first body and the second body being in a closed state with an inside of the first body facing an inside of the second body; the first body including a first guide wire sandwiching and holding portion, and the second body including a second guide wire sandwiching and holding portion; at least a part of the distally exposed portion of the guide wire being in contact with, and being sandwiched and held by, the first guide wire sandwiching and holding portion and the second guide wire sandwiching and holding portion; the first body including a first tube body sandwiching and holding portion and the second body including a second tube body sandwiching and holding portion, the distal end portion of the tube body being in contact with, and being sandwiched and held by, the first tube body sandwiching and holding portion and the second tube body sandwiching and holding portion; whereby a distal-most end of the guide wire is positioned within the protector;

the protector in the closed state being openable to an open state in which the first and second bodies are relatively moved away from each other so that the part of the distally exposed portion of the guide wire is no longer sandwiched and held by the first guide wire sandwiching and holding portion and the second guide wire sandwiching and holding portion, and so that the distal end portion of the tube body is no longer sandwiched and held by the first tube body sandwiching and holding portion and the second tube body sandwiching and holding portion;

wherein said first body includes a first engagement portion comprising a rib portion and said second body includes a second engagement portion comprising a concave portion, said first engagement portion frictionally engaging the second engagement portion in the closed state; and wherein said first engagement portion substantially surrounds the first guide wire sandwiching and holding portion and said second engagement portion substantially surrounds the second guide wire sandwiching and holding portion such that, in the closed state, a distal-most end of the guide wire is completely covered.

2. The protector according to claim 1, wherein
the distal portion of the guide wire possesses a curved shape in a natural state of the guide wire when an external force is not applied to the distal portion of the guide wire, and
the first guide wire sandwiching and holding portion and the second guide wire sandwiching and holding portion sandwich and hold the distal portion of the guide wire while maintaining the curved shape of the distal portion of the guide wire.

3. The protector according to claim 1, wherein
the first tube body sandwiching and holding portion is provided on the inside of the first body,
the second tube body sandwiching and holding portion is provided on the inside of the second body, and
at least one of the first tube body sandwiching and holding portion and the second tube body sandwiching and holding portion includes a groove in which is positioned the distal end portion of the tube body.

4. The protector according to claim 1, wherein
the first tube body sandwiching and holding portion includes a groove on the inside of the first body, and the second tube body sandwiching and holding portion includes a groove on the inside of the second body, the groove on the inside of the first body being longitudinally spaced from the groove on the inside of the second body, and
one part of the distal end portion of the tube body being positioned in the first groove and an other part of the distal portion of the tube body being positioned in the second groove, the one part of the distal portion of the longitudinal groove being longitudinally shifted relative to the other part of the distal potion of the tube body along a longitudinal extent of the tube body.

5. A protector used to cover a distal portion of a guide wire protruding from a distal opening of a tube body comprising:
a first half body and a second half body positionable in both a closed state in which an inside of the first half body faces an inside of the second half body and an open state in which the inside of the first half body and the inside of the second half body are exposed;
the first half body including a first guide wire sandwiching and holding portion and the second half body including a second guide wire sandwiching and holding portion, the first guide wire sandwiching and holding portion and the second guide wire sandwiching and holding portion being configured to receive the distal portion of the guide wire and sandwich and hold the distal portion of the guide wire in the closed state of the protector;
the first half body including a first tube body sandwiching and holding portion and the second half body including a second tube body sandwiching and holding portion, the first tube body sandwiching and holding portion and the second tube body sandwiching and holding portion being configured to sandwich and hold the tube body in the closed state of the protector; and
the first half body including a first engagement portion and the second half body including a second engagement portion, the first engagement portion comprising a rib portion and the second engagement portion comprising a concave portion, said first engagement portion frictionally engaging the second engagement portion in the closed state;
wherein said first engagement portion substantially surrounds the first guide wire sandwiching and holding portion and said second engagement portion substantially surrounds the second guide wire sandwiching and holding portion such that, in closed state, a distal-most end of the guide wire is completely covered; and
wherein the first tube body sandwiching and holding portion and the second tube body sandwiching and holding portion extend along a portion of a longitudinal axis of the protector, the longitudinal axis of the protector intersecting the first engagement portion and the second engagement portion in the closed state.

6. The protector according to claim 5, wherein
the first guide wire sandwiching and holding portion is provided on the inside of the first half body, and
the second guide wire sandwiching and holding portion is provided on the inside of the second half body.

7. The protector according to claim 5, wherein the first guide wire sandwiching and holding portion and the second guide wire sandwiching and holding portion are each constituted by flat surfaces facing each other in the closed state of the protector.

8. The protector according to claim 5, wherein the first guide wire sandwiching and holding portion includes a projecting portion and the second guide wire sandwiching and holding portion includes a recessed portion, the projecting portion being positioned in the recessed portion in the closed state of the protector.

9. The protector according to claim 5, wherein the first guide wire sandwiching and holding portion includes a projecting portion and the second guide wire sandwiching and holding portion includes a recessed portion, the projecting portion and the recessed portion facing each other in the closed state of the protector, and an elastically deformable groove is formed at a top portion of the projecting portion.

10. The protector according to claim 5, wherein
the first tube body sandwiching and holding portion is provided on the inside of the first half body, and
the second tube body sandwiching and holding portion is provided on the inside of the second half body.

11. The protector according to claim 5, wherein
the first tube body sandwiching and holding portion is a groove on the inside of the first half body, and
the second tube body sandwiching and holding portion is a groove on the inside of the second half body.

12. The protector according to claim 11, wherein the groove on the inside of the of the first half body is longitudinally shifted relative to the groove on the inside of the second body half along a longitudinal extent of the first and second half bodies so that the groove on the inside of the first half body and the groove on the inside of the second body half are arranged to receive different portions of the tube body in the longitudinal direction of the tube body.

13. The protector according to claim 11, wherein the groove on the inside of the first half body and the groove on the inside of the second body half possess different cross-sectional shapes.

14. The protector according to claim 5, wherein
the first engagement portion is constituted by a projecting portion and the second engagement portion is constituted by a recessed portion, the projecting portion being positioned in the recessed portion in the closed state of the protector by inserting the projecting portion into the recessed portion in an insertion direction, and
the first engagement portion is elastically deformed in a direction perpendicular to the insertion direction when the projecting portion is positioned in the recessed portion.

15. The protector according to claim 14, further comprising: an operation unit for release-operating the closed state maintained by the locking unit, the operation unit comprising a peripheral portion of one of the first and second half bodies extending outwardly beyond an outer periphery of an overlapping portion of the other of the first and second half bodies.

16. The protector according to claim 5, wherein the first half body and the second half body are connected by together by a rotation supporting portion so that one of the first and second half bodies is rotatable relative to the other of the first and second half bodies.

17. The protector according to claim 5, wherein the first half body and the second half body are integrally formed as a one piece unit.

18. The protector according to claim 5, wherein the first guide wire sandwiching and holding portion comprises a flexible surface which is deformable by the distal portion of the guide wire when the guide wire is positioned between the inside of the first half body and the inside of the second half body while the protector is in the closed state.

19. A method of protecting a distal portion of a guide wire protruding from a distal opening of a tube body comprising:
positioning the distal portion of the guide wire which is protruding from the distal opening of the tube body between a first body of a protector and a second body of the protector while the first and second bodies are in an open state, the first body including a first guide wire sandwiching and holding portion and a rib portion substantially surrounding the first guide wire sandwiching and holding portion and the second body including a second guide wire sandwiching and holding portion and a concave portion substantially surrounding the second guide wire sandwiching and holding portion; and
moving the first and second bodies to a closed state in which the first body overlaps the second body so that the distal portion of the guide wire is sandwiched and held between the first guide wire sandwiching and holding portion and the second guide wire sandwiching and holding portion and the rib portion frictionally engages the concave portion so that a distal-most end of the guide wire is completely covered and protected inside the protector;
wherein the first body includes a first tube body sandwiching and holding portion and the second body includes a second tube body sandwiching and holding portion, and the method further comprising sandwiching and holding a distal portion of the tube body between the first tube body sandwiching and holding portion and the second tube body sandwiching and holding portion when the first and second bodies are moved to the closed state.

20. The protector according to claim 1, wherein the first guide wire sandwiching and holding portion comprises a first groove and said second guide wire sandwiching and holding portion comprises a second grove, the first groove and the second groove having different curvatures.

21. The protector according to claim 20, wherein the curvature of the first groove is greater than the curvature of the second groove.

* * * * *